(12) United States Patent
Kosh et al.

(10) Patent No.: US 7,510,345 B2
(45) Date of Patent: Mar. 31, 2009

(54) QUICK RELEASE ASSEMBLY

(75) Inventors: Matthew Kosh, Seattle, WA (US); John N. Tilden, Bellevue, WA (US)

(73) Assignee: Bodypoint Designs, Inc., Seattle, WA (US)

( * ) Notice: Subject to any disclaimer, the term of this patent is extended or adjusted under 35 U.S.C. 154(b) by 296 days.

(21) Appl. No.: 11/084,761

(22) Filed: Mar. 18, 2005

(65) Prior Publication Data

US 2005/0207837 A1    Sep. 22, 2005

Related U.S. Application Data

(60) Provisional application No. 60/554,195, filed on Mar. 18, 2004.

(51) Int. Cl.
*F16B 21/02*   (2006.01)
(52) U.S. Cl. .................. 403/330; 403/322.3; 403/325; 403/328; 292/49; 292/197; 292/224
(58) Field of Classification Search ............. 403/321, 403/322.1, 322.3, 325, 322.4, 326, 328, 330, 403/409.1; 292/49, 53, 197, 224, 227
See application file for complete search history.

(56) References Cited

U.S. PATENT DOCUMENTS

| 1,074,615 | A |   | 10/1913 | Folmer |
|-----------|---|---|---------|--------|
| 1,527,754 | A |   | 2/1925  | Simon |
| 1,818,442 | A |   | 8/1931  | Widmer |
| 2,658,777 | A | * | 11/1953 | Rauglas ............ 403/104 |
| 3,002,774 | A | * | 10/1961 | Chapellier .......... 403/325 |
| 3,640,571 | A |   | 2/1972  | Keropian |
| 3,704,910 | A |   | 12/1972 | Willcott |
| 4,004,486 | A |   | 1/1977  | Schenk |
| 4,065,179 | A |   | 12/1977 | Takasaki |
| 4,073,537 | A |   | 2/1978  | Hammersburg |
| 4,650,529 | A |   | 3/1987  | Guest |

(Continued)

FOREIGN PATENT DOCUMENTS

CH    622 421    * 12/1978

(Continued)

OTHER PUBLICATIONS world.altavista.com online Babel Fish translation: Schwarze et al. (FR 1,002,404).*

*Primary Examiner*—Michael P Ferguson
(74) *Attorney, Agent, or Firm*—Townsend and Townsend and Crew LLP

(57) ABSTRACT

A pivoting side mount (26) which may used, for example, to attach a pelvic stabilization device (21) to a wheelchair. The pivoting side mount (26) includes first and second pivot brackets (152, 150) that are rotatably connected to one another and a spring (154), such as a rubber spring, for limiting the rotating movement of the two brackets relative to one another. A quick release assembly (28) is also provided. The quick release assembly (28) includes a receiver (30) and a body (40) that fits into the receiver. The body (40) includes one or more latches (42) that are biased outward and that snap into notches (44) in the receiver (30) when the body (40) is placed in the receiver (30). A release plate (46) is provided for releasing the latch or latches (42) from the notches (44).

23 Claims, 14 Drawing Sheets

U.S. PATENT DOCUMENTS

| | | | |
|---|---|---|---|
| 4,813,746 A | | 3/1989 | Mulholland |
| 4,981,307 A | | 1/1991 | Walsh |
| 5,439,310 A | * | 8/1995 | Evenson et al. ............. 403/321 |
| 5,447,356 A | | 9/1995 | Snijders |
| 5,548,879 A | * | 8/1996 | Wu .............................. 24/625 |
| 5,564,788 A | | 10/1996 | Warhaftig |
| 5,611,638 A | * | 3/1997 | Dorr et al. .................. 403/321 |
| 5,678,798 A | | 10/1997 | Little |
| 6,041,479 A | | 3/2000 | Colpo et al. |
| 6,213,558 B1 | | 4/2001 | Axelson et al. |
| 7,144,180 B2 | * | 12/2006 | Stahle et al. ............. 403/109.1 |

FOREIGN PATENT DOCUMENTS

| | | |
|---|---|---|
| DE | 204579 C | 8/1939 |
| DE | 929442 C | 6/1955 |
| EP | 0 444 185 B | 5/1994 |
| EP | 0 546 967 B1 | 3/1995 |
| FR | 934068 A | 5/1948 |
| FR | 948706 A | 8/1949 |
| FR | 1002404 A | 3/1952 |
| GB | 978999 A | 1/1965 |

\* cited by examiner

1

QUICK RELEASE ASSEMBLY

REFERENCE TO RELATED APPLICATION

This patent application claims priority to U.S. provisional Patent Application No. 60/554,195, filed Mar. 18, 2004, and entitled "PIVOTING SIDE MOUNT AND QUICK RELEASE ASSEMBLY FOR A PELVIC STABILIZATION DEVICE," incorporated herein by reference.

TECHNICAL FIELD OF THE INVENTION

The present invention is directed to ambulatory support devices, and more specifically to a pelvic stabilization device.

BACKGROUND OF THE INVENTION

Maintaining a proper pelvic posture and providing stability through the pelvis are critical to overall sitting posture. Freedom of movement can be enhanced by achieving a stable base of support. The optimum position for the pelvis is a slight anterior tilt. An effective pelvic support will prevent the pelvis from tilting posteriorly. A posterior pelvic tilt promotes rounding of the upper spine, which can lead to deformity. For a pelvis which posteriorly tilts, the top of the pelvis must be blocked from moving back and the bottom of the pelvis must be stabilized from moving forward. With adequate proximal support, less support is required distally. Therefore, with increased stability of the pelvis, the user is less dependent upon additional supports in order to maintain a functional, upright sitting posture. Individuals using wheelchairs need assistance to maintain pelvic stability.

The neutral posture of the pelvis is a dynamic state which should be allowed to move. Therefore, a rigidly stabilizing pelvic position is not desirable. Currently available pelvic supports either do not control undesired pelvic movement, or lock the pelvis in a static, non-functional position. Movements of the pelvis are critical to maintaining an active posture and should not be rigidly stabilized.

U.S. Pat. No. 6,213,558 (the "'558 patent") discloses a pelvic stabilization device that attaches to a wheelchair and includes a pelvic support brace and an apparatus for attaching the pelvic support brace to the wheelchair. A pivot apparatus provides movement of the pelvic support brace with respect to the apparatus for attaching the pelvic support brace, the pelvic support brace being pivotable between a first, neutral position and a second, tilted position. A pivot return apparatus is attached to the pelvic support brace to return the pelvic support brace to the first, neutral position from the second, tilted position. A pivot limiting apparatus resists the amount of pivot of the pelvic support brace that is inducible by the pivot apparatus.

The pelvic stabilization device in the '558 patent includes a padded rear shell, two padded front shells, lateral hip pads, a pivot mechanism, a pivot limiter, a fore-aft lock, and attachment hardware. The rear shell supports the pelvis at the sacrum, the posterior superior iliac spines (PSIS's) and the sides of the pelvis. The width of the rear shell is adjustable to provide a custom fit for each user. The two front shells support the front of the pelvis at and around the anterior superior iliac spines (ASIS's). Lateral hip pads at the greater trochanter are designed to prevent the pelvis from sliding to the sides.

The pivot mechanism in the '558 patent allows anterior and posterior tilting of the pelvis. Adjustable centering springs help return the pelvis back to a neutral position and provide dynamic resistance to pelvic movement. The pivot limiter allows pivot movement of the pelvic stabilization device, and the user's pelvis, for only a predetermined range of motion. A separate adjustment for anterior and posterior tilt ranges allows adjustment of one independently of the other. The pivot limiter can be a mechanism separate from the pivot mechanism or, alternatively, the pivot limitation can be accomplished by the pivot mechanism. The pivot mechanism itself can limit pivot movement when, for example, the pivot mechanism is a spring, elastomeric or piston device. Pivot movement is then limited by the amount of force the user can provide against the pivot mechanism and still attain pivoting movement.

SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment of the invention, a pivoting side mount is provided which may used, for example, to attach a pelvic stabilization device to a wheelchair. The pivoting side mount includes first and second pivot brackets that are rotatably connected to one another and a spring, such as a rubber spring, for resisting that rotating movement of the two brackets relative to one another. The spring constant for the rubber spring may be selected for a desired application, for example, the weight and/or ambulation of a user in the wheelchair. In addition, in accordance with an embodiment, the pivoting side mount is configured and arranged so that the rubber spring may be changed or replaced by an operator.

In accordance with an embodiment, the pivoting side mount attaches to the pelvic stabilization device in a manner such that the height of the pelvic stabilization device may be adjusted. For example, the pivoting side mount may include a height adjustment bar that permits sliding movement of the pelvic stabilization device relative to the pivoting side mount. In an embodiment, the height adjustment bar is round and is part of a T-bar. The T-bar is attached in a pivoting manner to a mounting plate that attaches to the pelvic stabilization device, permitting compensation from misalignment of attachment of the pivoting side mount in three axes. That is, the pivoting side mount may be adjusted relative to the mounting plate in two dimensions (up and down and rotation), and the pivoting side mount may swing outward from the mounting plate.

In accordance with another embodiment, a quick release assembly is provided. The quick release assembly includes a receiver and a body that fits into the receiver. The body includes one or more latches that are biased outward and that snap into notches in the receiver when the body is placed in the receiver. In accordance with an embodiment, a release plate is provided for releasing the latch or latches from the notches.

In accordance with an embodiment, each of the latches is biased outward and includes a rounded cam surface which engages a respective notch so as to bias the body into the receiver. In addition, the rounded cam surface is positioned and configured so that it continues to bias the body into the receiver and attach the body to the receiver after some wear of the cam surface and/or the respective notch. In an embodiment, to provide this function the latch is initially arranged so that it engages the notch at a midpoint along the rounded cam surface, and wear causes the cam surface to be engaged at a location further along the rounded cam surface.

In accordance with an embodiment, the release plate includes a lock which prevents undesired release of the body from the receiver. In an embodiment, the lock is re-positionable from a locked position to an unlocked position.

Other features of the invention will become apparent from the following detailed description when taken in conjunction with the drawings, in which:

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. In addition, to the extent that orientations of the embodiments are described, such as "top," "bottom," "front," "rear," "right," and the like, the orientations are to aid the reader in understanding the embodiment being described, and are not meant to be limiting.

Figure 1:
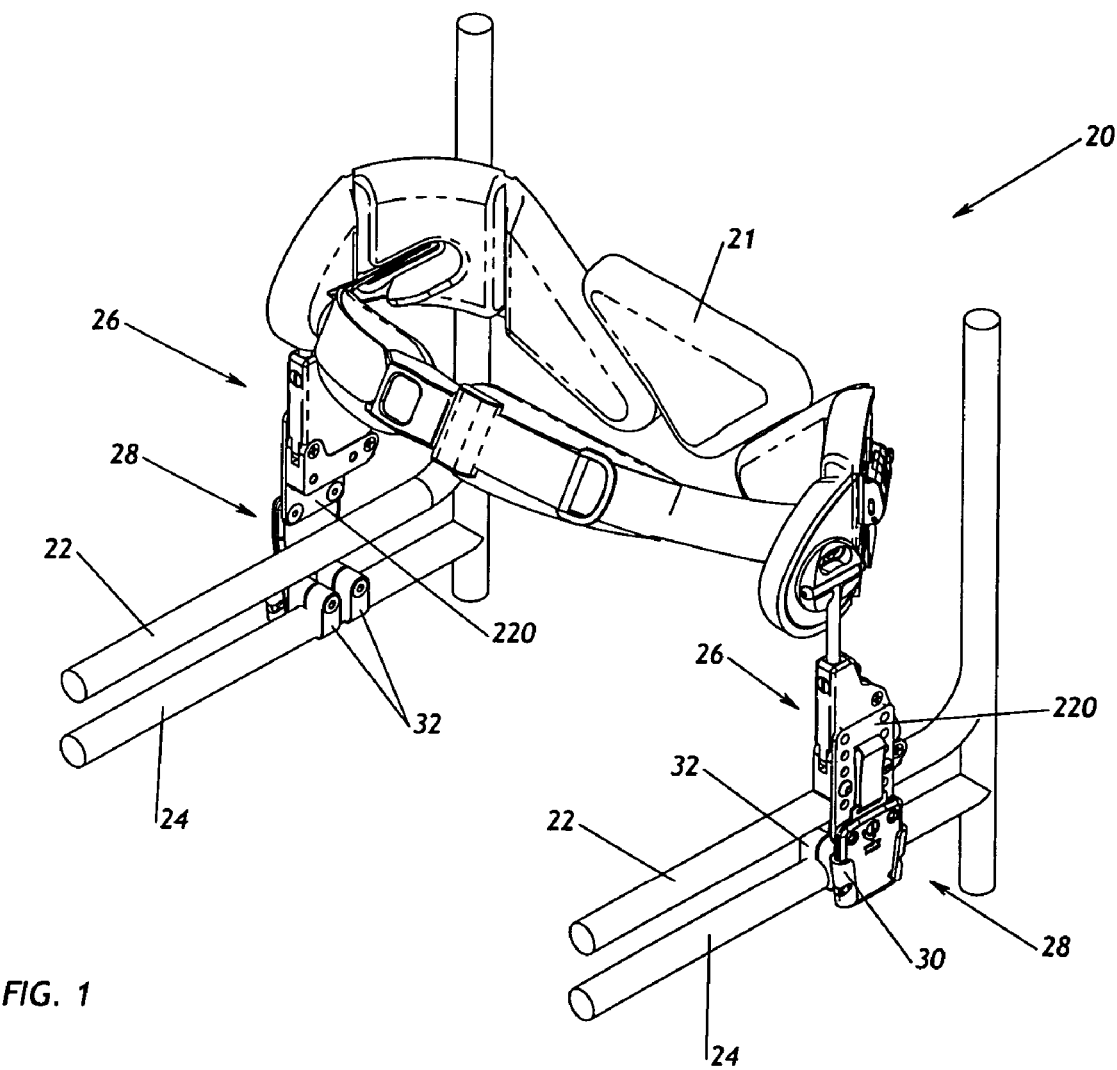
FIG. 1 is a side perspective view of a pelvic stabilization device and associated attachment hardware, specifically a pivoting side mount and quick release assembly, in accordance with an embodiment of the invention.

Referring now to the drawings, in which like reference numerals represent like parts throughout the several views, FIG. 1 shows a pelvic stabilization device 20 incorporating an embodiment of the invention. The pelvic stabilization device 20 includes a pelvic support brace 21 similar to the pelvic support brace designated by the reference numeral 10 in the '558 patent. In addition, the pelvic stabilization device 20 may include many of the other features of the pelvic stabilization device 2 of the '558 patent, but many of those features are not shown in the drawings so as to not obfuscate the invention. For example, the pelvic stabilization device may include a pad securing strap, front pads, rear pads, and related mounts such as are described in the '558 patent.

In accordance with an embodiment of the invention, the pelvic support brace 21 is attached to wheelchair sidebars 22, 24 by a novel pivoting side mount 26. One each is positioned on the opposite sides of the pelvic stabilization device 20. In addition, a quick release assembly 28 is provided for attaching each of the pivoting side mounts 26 to the wheelchair sidebars 22, 24. Again, one each is positioned on the opposite sides of the pelvic stabilization device 20, in the shown embodiment just underneath the pivoting side mounts 26. In the embodiment shown, an adapter plate 220 serves as an adjustable connection between the pivoting side mount 26 and the quick release assembly 28, although they may be directly connected or connected in another manner. The pivoting side mount 26 and the quick release assembly 28 are each further described below.

Although described with reference to attachment of the pelvic support brace 21, the quick release assembly 28 may be used for a variety of applications for which attachment is desired. As nonlimiting examples, the quick release assembly 28 may be used for a quick release buckle for harnesses or on cargo holding systems, a quick release attachment for a gunsight to artillery, or a detachable mount for a camera or lighting.

Likewise, while the pivoting side mount 26 is described with reference to the pelvic support brace 21, the pivoting side mount may alternatively be used for any connection between two elements where bending at the connection is desired, with a bias toward one position and a resistance to lateral movement. For example, the pivoting side mount 26 may be used as a spring tensioner for ski bindings, on office chairs, or on exercise equipment. Also, the pivoting side mount 26 may be attached by a way other than quick release assembly 28. The pivoting side mount 26 may also attach directly to a wheelchair, or may include an intermediate structure, such as the adapter plate 220.

The quick release assembly 28 includes a receiver 30 (best shown in FIG. 2) that attaches by a pair of clamps 32 (FIG. 1) to the wheelchair sidebars 22, 24. A quick release assembly 28 and associated receiver 30 are mounted on each of the opposite wheelchair sidebars 22, 24, and for ease of description, only one quick release assembly 28 is described.

Referring again to FIG. 2, the receiver 30 includes mounting holes 34 at a back portion of the receiver 30 and side channels 36 along each side edge of the receiver 30. The mounting holes 34 are arranged and positioned to receive fasteners (not shown, but known), for example, for attaching to the clamps 32. The receiver 30 may be attached to a structure in a different way, such as by welding, gluing, straps, rivets, or another suitable manner.

Figure 2:
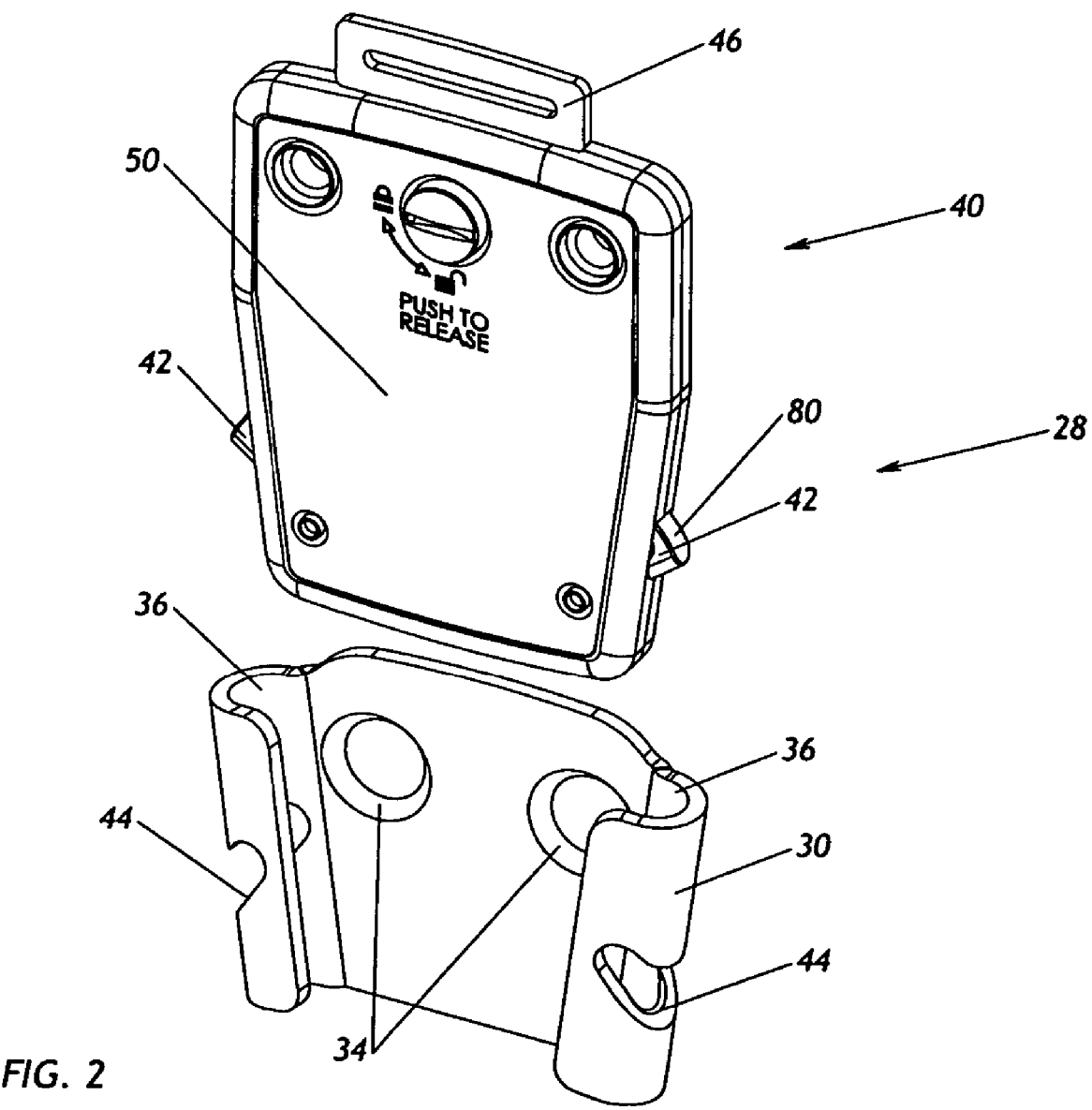
FIG. 2 is a side perspective view of a quick release assembly for use with the pelvic stabilization device of FIG. 1, with the quick release assembly shown in a detached state.

As can be seen in FIG. 2, the quick release assembly 28 includes a body 40 that fits within the receiver 30. In the embodiment shown, the body 40 is connected to the pelvic support brace 21. More specifically, the body 40 attaches to a bottom portion of the pivoting side mount 26, which in turn is attached to the pelvic support brace 21. Alternatively, a separate adapter plate 220 may be provided between the body 40 and the pivoting side mount 26. The adapter plate 220 may be, for example, a stamped flat or bent steel plate which accommodates great height or width adjustments or unusual installation requirements.

The body 40 includes latches 42 extending out of side, bottom edges of the body 40. The latches 42 are positioned and arranged to engage notches 44 in the side channels 36 of the receiver 30. A release plate 46 is provided for removing the latches 42 from the notches 44.

Figure 3:
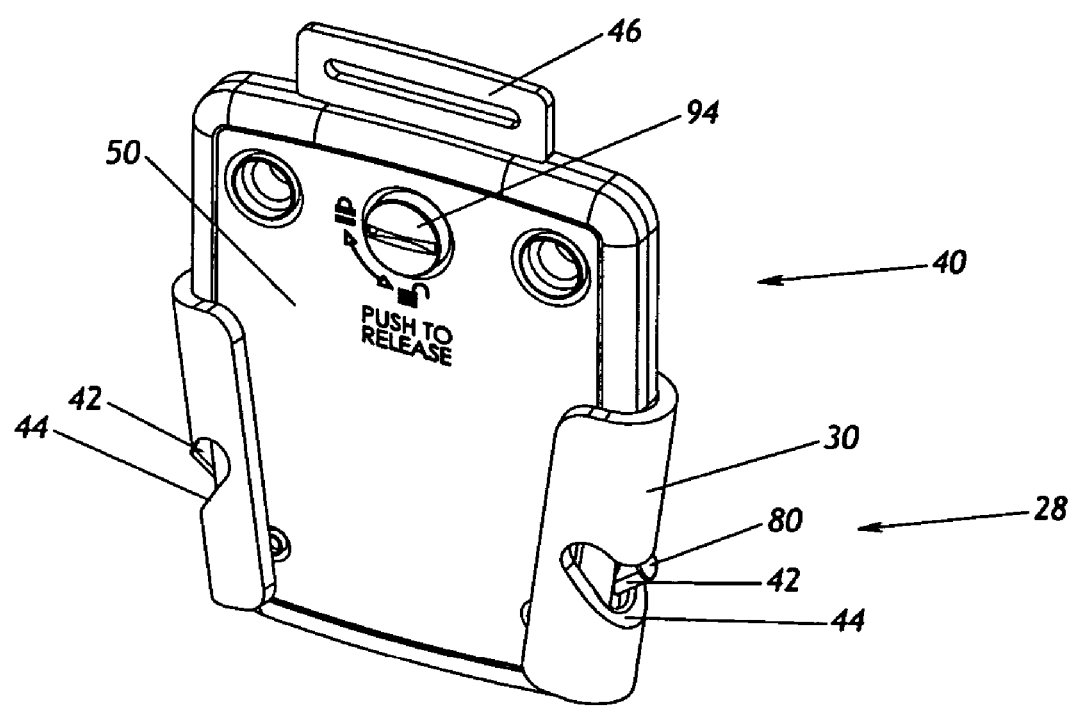
FIG. 3 is a side perspective view of the quick release assembly of FIG. 2, with the quick release assembly in an attached state.
Figure 4:
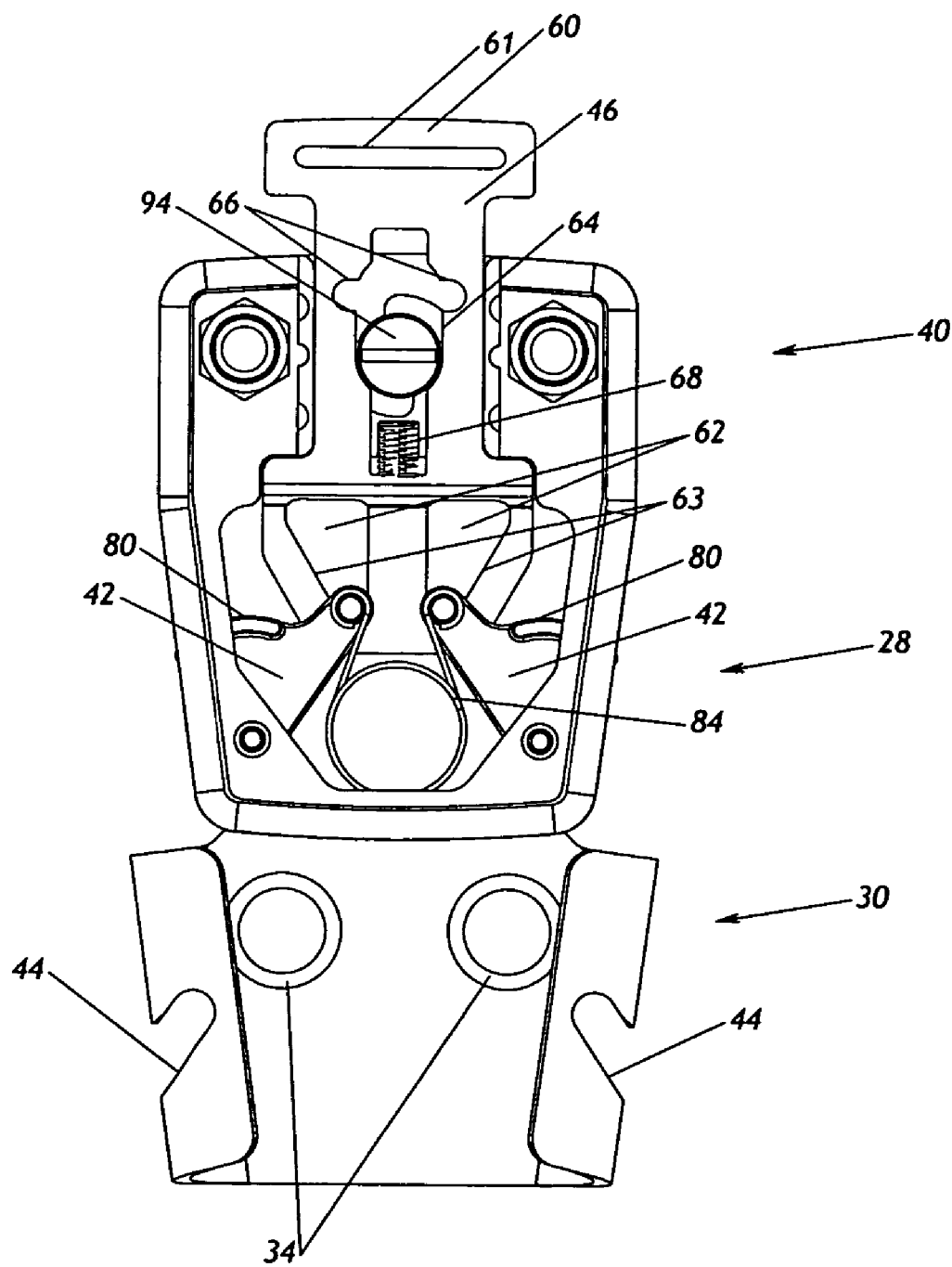
FIG. 4 is a front view of the quick release assembly of FIG. 2, with the quick release assembly in a detached state and with a release plate for the quick release assembly engaged, and a front plate of a body for the quick release assembly removed to show detail.
Figure 5:
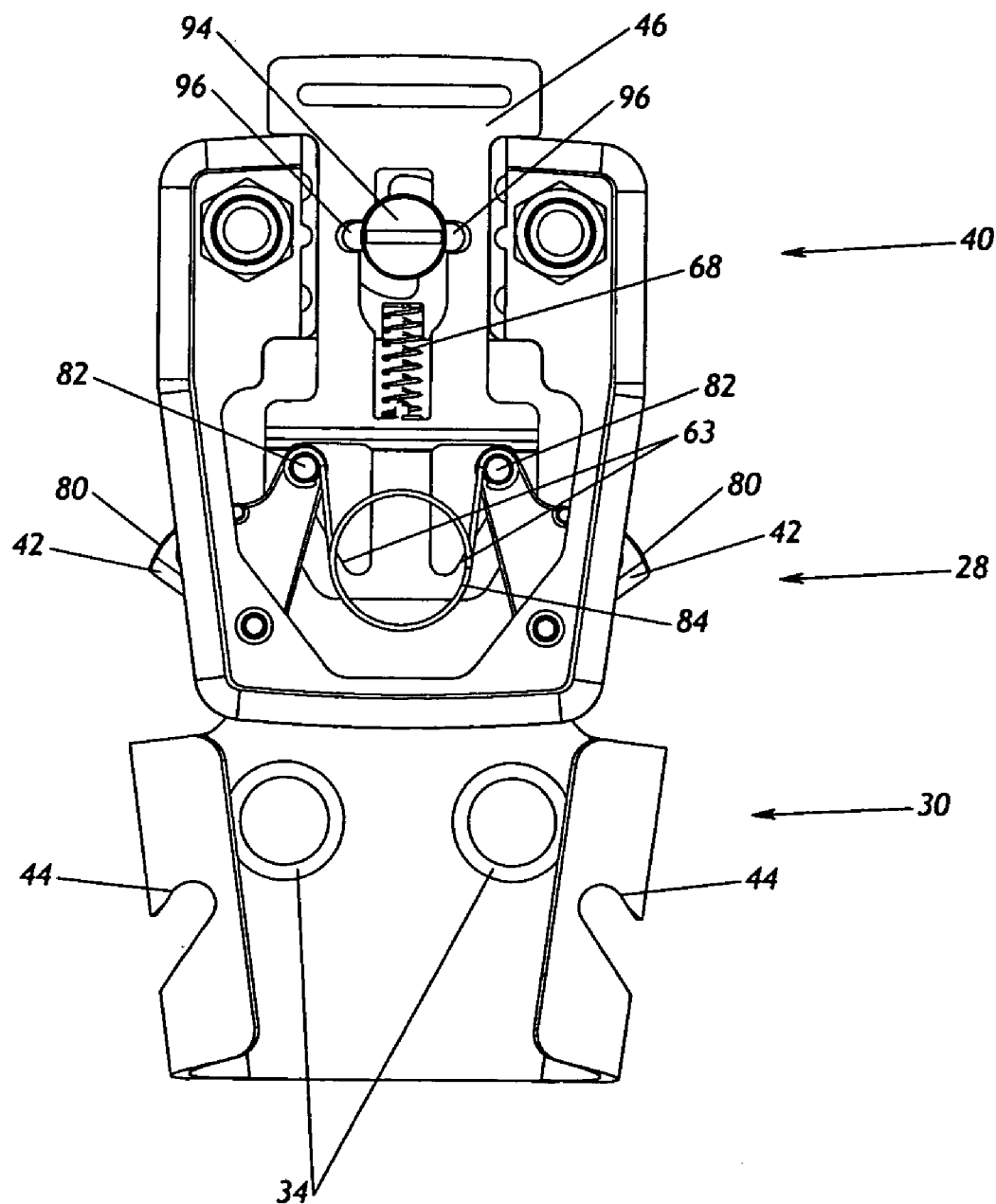
FIG. 5 is a front view of the quick release assembly of FIG. 2, similar to FIG. 4, but with the release plate released.

Although the structure and operation of the quick release assembly 28 will be described in further detail below, a general description is given here for the benefit of the reader. As can be seen in FIG. 3, the body 40 fits into the receiver 30, with the latches 42 extending outward and engaging the notches 44. A user may pull up on the release plate 46 (to the position shown in FIG. 4) to cause the latches 42 to rotate inward out of alignment with the notches 44. The user may then pull the body 40 out of the receiver 30, as is shown in FIG. 4. If desired, the user may then release the release plate 46, causing the latches 42 to extend out of the sides of the body 40, as is shown in FIG. 5.

To re-insert the body 40 into the receiver, a user simply presses the body 40 down into the receiver 30. The release plate 46 does not have to be pulled upward, but it can be. If the release plate 46 is pulled upward, then the body 40 is simply inserted into the receiver 30, and the release plate is released, permitting the latches 42 to move outward into the notches 44.

Figure 7:
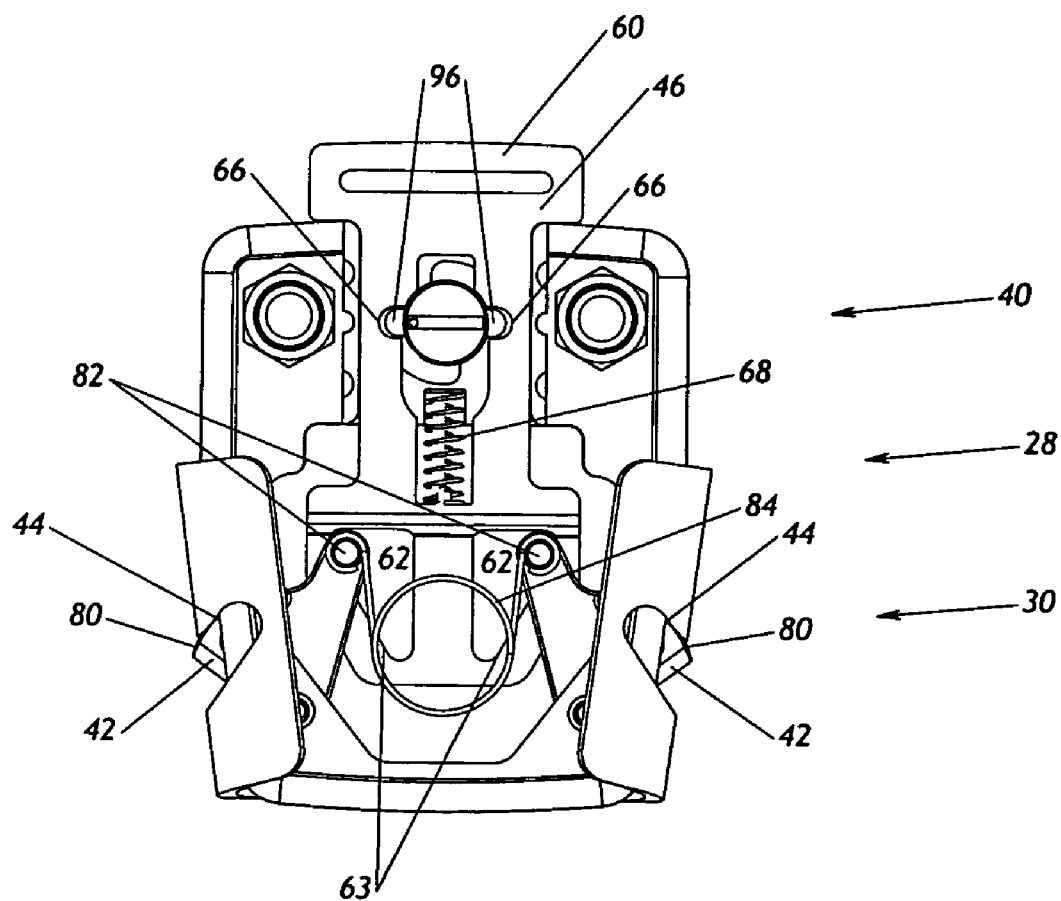
FIG. 7 is a front view of the quick release assembly of FIG. 2, similar to FIG. 6, shown fully inserted.

If the release plate 46 is not pulled upward when inserting the body 40, then the engagement of the latches 42 with the inside edges of the side channels 36 causes the latches 42 to pivot inward so that the body 40 may continue to be inserted into the receiver 30. Continued pressing of the body 40 downward into the receiver 30 causes the latches 42 to continue to rotate inward until the latches 42 engage the notches 44, at which time the latches 42 pivot outward and lock into position into the notches 44, such as is shown in FIG. 7. The body 40 is then latched again and returned to the position shown in FIG. 3.

Figure 8:
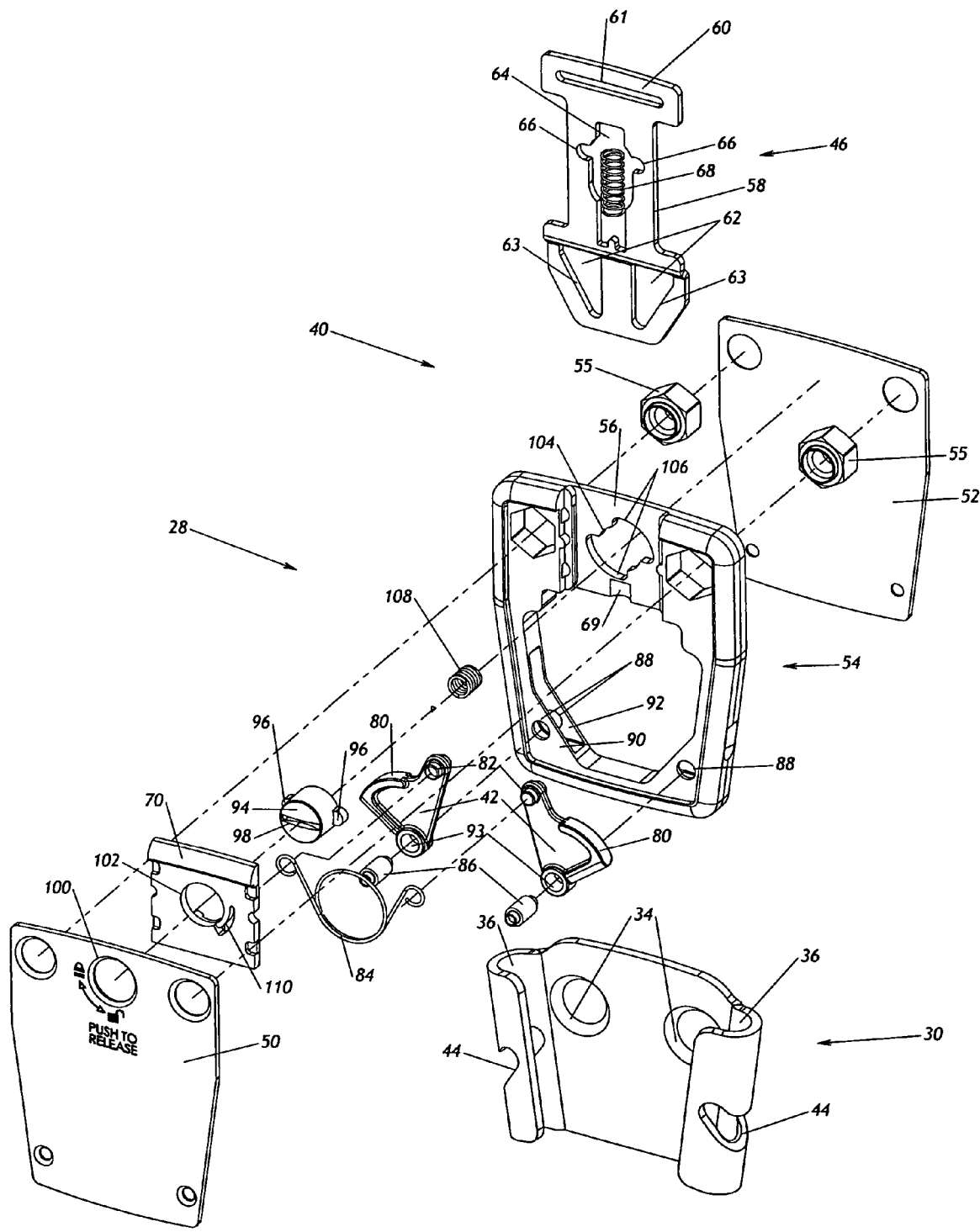
FIG. 8 is an exploded perspective view of the quick release assembly of FIG. 2.

FIG. 8 shows an exploded perspective view of the quick release assembly 28, and provides more detail of the structure of the body 40. In the embodiment shown, the body 40 includes a front cover 50 and a rear cover 52. A frame 54 is positioned between the front and rear covers 50, 52. Fasteners 55, such as nuts, fit into a top portion of the frame 54 and are captured between the front cover 50 and the rear cover 52. The fasteners 55 provide a structure to which a device may be attached, for example the pelvic stabilization device 20.

The frame 54 includes a slot 56 at an upper central portion. When assembled, a throat 58 of the release plate 46 fits into the slot 56 and is slidingly received therein.

The release plate 46 additionally includes a tab 60 at its upper end, with a strap slot 61 extending through the tab 60. Two openings 62 are located at the bottom of the release plate 46. Each opening 62 includes slanted inner cam surfaces 63 along inner edges thereof.

The release plate 46 also includes a center opening 64 having a pair of ear openings 66 extending out of side portions. A spring 68 is mounted in the center opening 64 and abuts a bottom portion of the center opening 64 and a cut-out 69 in the frame 54.

A filler plate 70 also fits into the slot 56. The filler plate 70 does not contact the throat 58 of the release plate 46 in the slot 56, but instead leaves a small gap to allow sliding of the release plate relative to the slot. The filler plate 70, as well as the front cover 50, are removed in FIGS. 4-7.

The latches 42 are generally triangular in shape and include rounded outer cam surfaces 80 along one edge, and pins 82 at upper corners thereof. A torsion spring 84 attaches to the pins 82 on the two latches 42, and is configured to force the two latches 42 apart. The pins 82 also extend rearwardly and into openings 62 so that the pins 82 may engage the slanted inner cam surfaces 63 of release plate 46.

The latches 42 are rotatably attached at pivot pins 86 that extend into holes 88 in the frame 54. Specifically, the holes 88 are positioned in front and rear walls 90, 92 at a bottom portion of the frame 54.

The latches 42 include holes 93 at one of the corners of the triangular shape. These holes 93 and the adjacent portion of the latches 42 are inserted between the front and rear walls 90, 92, and the pivot pins 86 are inserted to hold the latches 42 in place. The latches 42 are free to rotate about the pivot pins 86.

In an embodiment, a safety button 94 is supplied for the body 40. The safety button 94 includes ears 96 that align with the ear openings 66 in the center opening 64 of the release plate 46. The safety button 94 includes a slot 98, such as a tool receiving pattern or another pattern that allows a user to grip the safety button 94 to turn it, on its front face. The safety button 94 fits through an opening 100 in the front cover 50, through an opening 102 in the filler plate 70 and a third opening 104 in the frame 54. The third opening 104 includes extensions 106 formed in the shapes of arcs and extending approximately a quarter of the length around the opening 104 and on opposite sides of the opening 104. The extensions 106 are sized so that they can receive the ears 96 of the safety button 94, and permit the safety button to be rotated 90 degrees when the ears are received by the extensions 106. At the outer extremities of the 90 degree movement, the ears 96 engage the edges of the extensions.

A spring 108 is seated in the back of the safety button 94. The spring 108 abuts the rear cover 52 when the body 40 is assembled.

The body 40 may also be assembled without the safety button 94, omitting the safety button 94 and replacing the front cover with a cover similar to the rear cover 52 and having no hole.

Details of the operation of the body 40 can be seen in FIGS. 4-7. Beginning with FIG. 7, the body 40 is in a latched state with the latches 42 engaged in the notches 44 of the receiver 30. The rear portion of each of the pins 82 on the latches 42 engages an upper portion of the slanted inner cam surface 63 in the openings 62 on the release plate 46. The torsion spring 84 presses the cam surfaces 80 of the latches 42 outward. The spring 68 presses the release plate 46 into the downward position. The ears 96 on the safety button 94 engage the ear openings 66 on the release plate 46, preventing the release plate 46 from being pulled upward.

In this position, the safety button 94 is in a "locked" position. If desired, a user may unlock the safety button 94 to provide full function of the release plate 46. To do so, a user may press the safety button 94 inward against the bias of the spring 108 until the ears 96 are removed from alignment with the release plate 46 and are moved into alignment with the opening 104. At this position, the user may rotate the safety button ninety (90) degrees so that the ears 96 rotate within the extensions 106 (FIG. 8) until the ears are positioned upward and downward, thus preventing the ears from being pushed back into the ear openings 66 by the spring 108. Additional features may be provided for preventing the safety button 94 from accidental rotation back into a locked position. For example, when the safety button 94 has been rotated to a position where the ears 96 are aligned upward and downward, the spring 108 may force the ears into pockets (not shown)

incorporated into the back of the filler plate 70. These pockets prevent rotation of the safety button 94 unless a user presses the safety button inward against the bias of the spring 108.

In any event, at the "unlocked" position of the safety button 94, a user may pull upward on the release plate 46 at any time. If desired, a spring section 110 (FIG. 8) may be provided in the filler plate 70 that acts against notches or other structures (not shown) on the periphery of the safety button 94 to offer sensory feedback to a user when turning the safety button 94 between the locked and unlocked positions, and ensuring that a selected position of the safety button 94 (locked or unlocked) is maintained under vibration.

If, however, the safety button 94 is in the locked position shown in FIG. 7, then to pull the release plate 46 upward, a user presses the safety button 94 inward against the bias of the spring 108 until the ears 96 on the safety button 94 have moved inward beyond the release plate 46, moving the ears 96 out of the paths of the ear openings 66 and thus out of the way of the release plate 46. The user may then lift the release plate 46 as long as the user is holding the safety button 94 inward. The user may release the safety button 94 as soon as the release plate has been moved far enough to misalign the ears 96 with the ear openings 66.

The release plate 46 is raised to remove the latches 42 from the notches 44. The user may raise the release plate 46 by grasping the tab 60 of the release plate 46 or, if desired, a strap 222 (FIG. 14) or other mechanism may be attached to the strap slot 61 for permitting remote release. This also allows for grasping with a gloved hand or aids grasping for users with diminished hand function.

When the user raises the release plate 46, the back side of the pins 82 travel along the slanted inner cam surfaces 63 at the bottom of the release plate 46, causing the latches 42 to pivot inward against the bias of the torsion spring 84. The user is lifting the release plate 46 against the bias of the spring 68. When the user has pulled upward on the release plate 46 a sufficient amount for the cam surfaces 80 on the latches 42 to release from the notches 44 on the receiver 30, the user may lift the body 40 out of the receiver 30.

Once the body 40 is released from the receiver 30, the release plate 46 may be released, returning the release plate 46 to the position shown in FIG. 5. Releasing the release plate 46 causes the spring 68 to pull the release plate 46 downward. At the same time, the torsion spring 84 presses outward on the pins 82 on the latches 42, and the pins 82 travel upward and outward along the slanted inner cam surfaces 63 on the bottom of the release plate 46. If the safety button 94 is in the "locked" position, then the ears 96 of the safety button 94 will snap back into the ear openings 66 on the release plate 46 when the release plate 46 is returned to its final position. Thus, the release plate 46 is once again locked in position.

Figure 6:
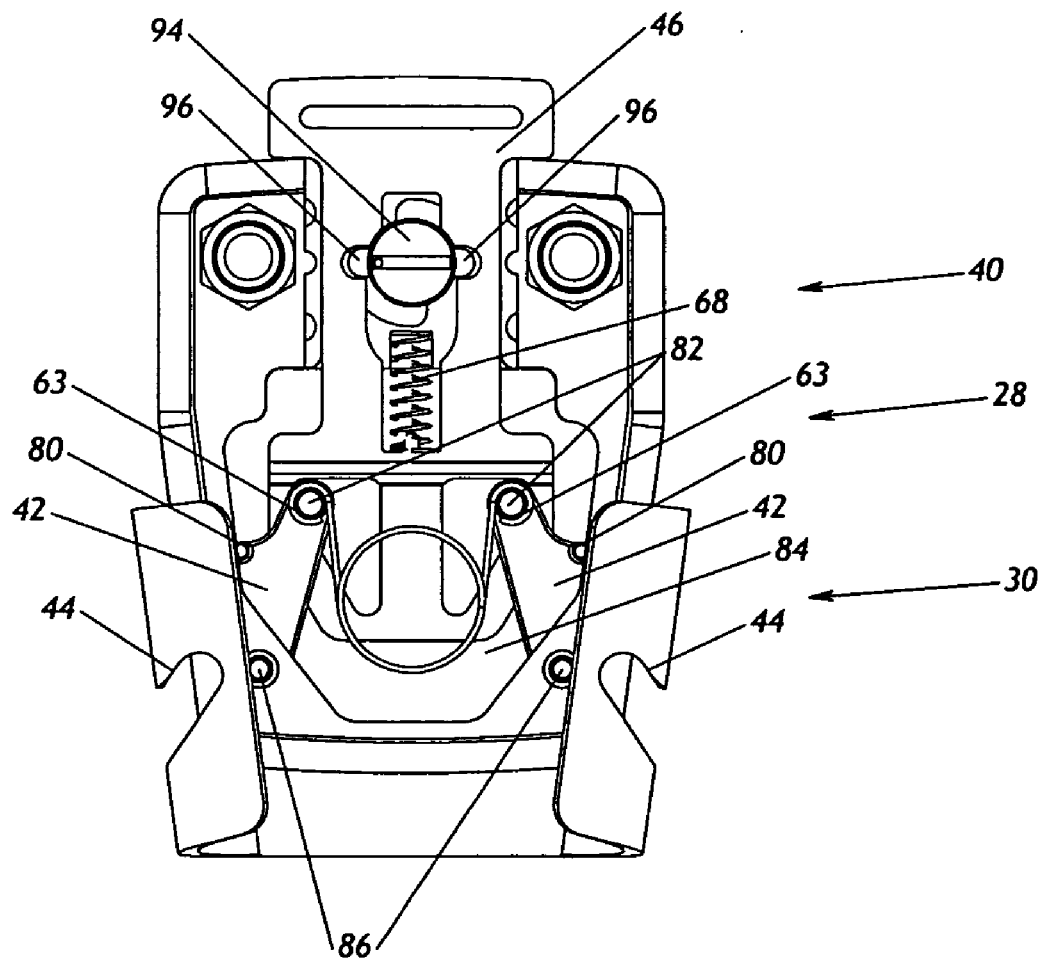
FIG. 6 is a front view of the quick release assembly of FIG. 2, similar to FIG. 5, with the body partially inserted into a receiver for the quick release assembly.

Although the release plate 46 is locked in position, movement of the release plate 46 is not required to re-insert the body 40 into the receiver 30. Instead, as shown in FIG. 6, the body 40 may be inserted in the receiver 30, and the latches 42 automatically pivot inward against the torsion spring 84 as a result of the outer edges of the outer cam surfaces 80 engaging the inner surfaces of the side channels 36 of the receiver 30. At this point, the pins 82 on the latches 42 release their contact with the slanted inner cam surfaces 63 of the release plate 46 and pivot inward to the position shown in FIG. 6. The user may then continue insertion of the body 40 into the receiver 30. The open shape of the receiver 30 allows dirt or other debris to fall through, preventing jamming of the body 40 upon insertion. In addition, the receiver 30 is tapered to ease entry of the body 40, enabling a user to easily insert the body 40 in place and to eliminate play over time as a result of manufacturing variations or wear to either the receiver 30 or the body 40. In addition, the outer edges of the body 40 are preferably radiused at frame 54 to match the curvature of the side channels 36 so as to provide automatic alignment of the receiver 30 and the body 40 in the fore and aft planes as well as left and right planes.

When the body 40 reaches the bottom of the receiver 30, the latches 42 spring outward due to the bias of the torsion spring 84 into the notches 44 on the receiver 30. The radiused edges of the body 40 are flattened at the extreme edges of frame 54 to provide additional clearance for debris and to ensure that flash from a molding operation will not interfere with the latching function of the body 40 and the receiver 30. The flattened edges also ensure that the body 40 engages the receiver 30 along only four sets of contact surfaces (the four corners of the body, two each engaging opposite sides of each side channel 36). The engagement of each set of contact surfaces resists movement in a different direction. These four different contact surfaces, in combination with the taper of the contact surfaces, eliminate play in both the fore and aft plane and the left and right plane.

Preferably, the latches 42 extend only part of the way out of the notches 44 when the body 40 is fully inserted in the receiver 30. That is, the pins 82 do not quite engage the slanted inner cam surfaces 63. This feature permits additional movement outward of the latches 42 to compensate for wear in the notches 44 and/or for normal manufacturing variations.

The outer cam surfaces 80 of the latches 42 are rounded so that each rounded surface acts against the flat surface of the respective notch 44 of the receiver 30. The pressure angle between the outer cam surfaces 80 and the notches 44 ensures that each latch 42 remains engaged against a load attempting to pull the body 40 free from the receiver 30. That is, the rounded nature of the cam surface 80 and the fact that it is slanted downward where it engages the notch 44 cause the latch 42 to be nearly in balance, so that an upward force neither causes the latches 42 to slip out of engagement or become more strongly engaged. This facilitates easy release of the mechanism while under load; i.e., allows a user to pull on the release plate 46 to separate the body 40 and the receiver 30 when desired. The latches 42 are kept engaged merely by friction and the outward force of the torsion spring 84.

As described above, the rounded surfaces of the outer cam surfaces 80 are slanted downward, meaning the distance from the outer surface of the outer cam surface 80 to the axis of rotation at the respective pivot pin 86 decreases as the outer surface moves from the inward end of the respective latch 42 toward the outer end. This feature, shown in FIGS. 5 and 8, provides the "cam" function of the outer surface.

The rounded surfaces of the outer cam surfaces 80 not only compensate for wear as described above, but also, due to the cam action, the rounded surfaces, because they are slanted downward and are biased outward, tend to pull the body 40 into full engagement with the receiver 30, forcing the body 40 into the receiver 30 and wedging it into a position so as to prevent lateral motion between the receiver 30 and the body 40. That is, the torsion spring 84 pushes outward on the latches 42, causing the cam surfaces 80 to press outward into the notches 44 as far as possible, causing the notches 44 to "crawl" up the cam surfaces, forcing the body 40 downward into the receiver 30.

Figure 9:
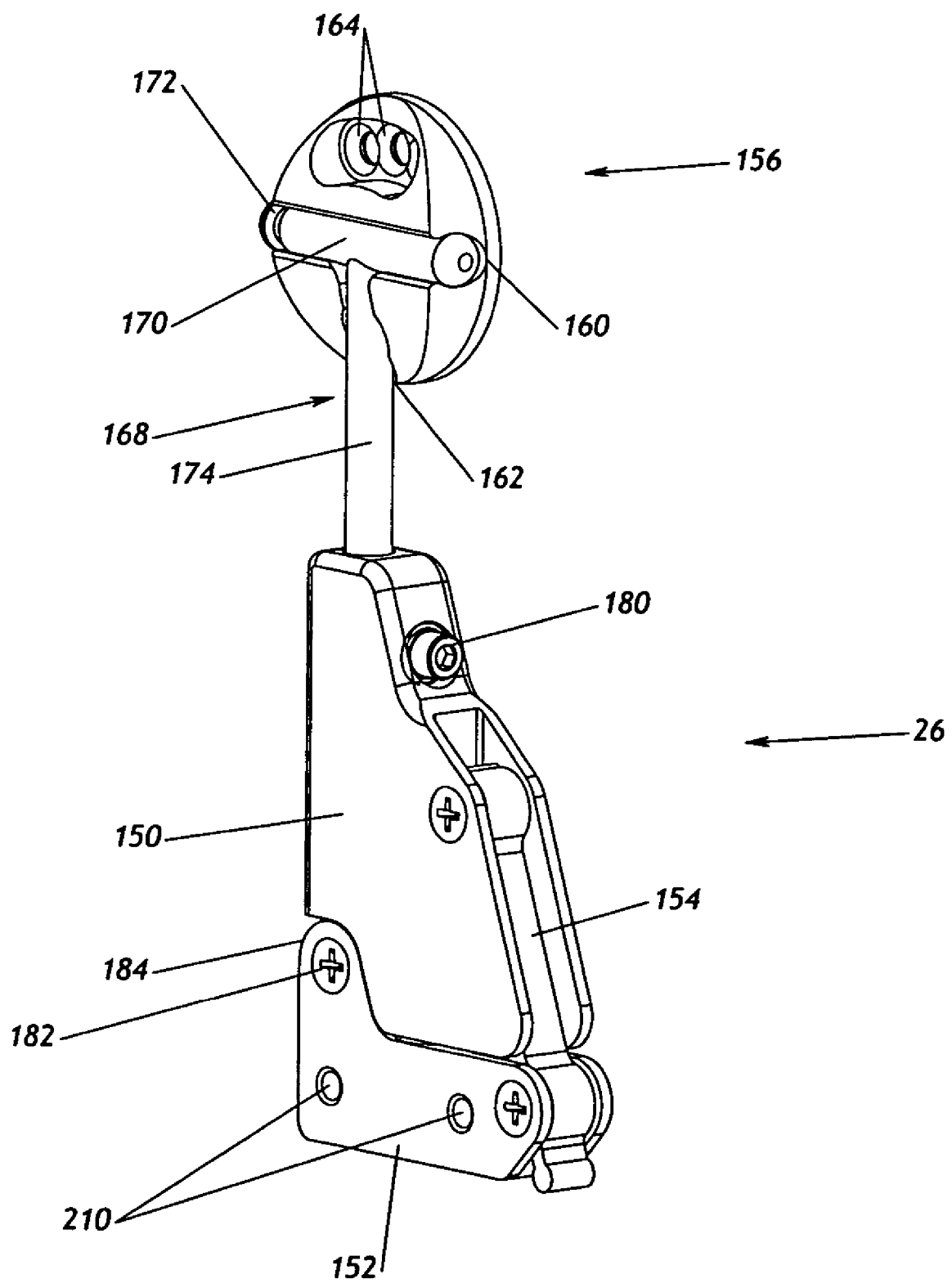
FIG. 9 is a side perspective view of the pivoting side mount of FIG. 1.

FIG. 9 shows detail of the pivoting side mount 26. The pivoting side mount 26 includes an upper pivot bracket 150 mounted above a lower pivot bracket 152. In accordance with an embodiment, the upper pivot bracket 150 is rotatable relative to the lower pivot bracket 152. A spring, in the embodiment shown, a rubber spring 154, resists the rotation of the upper pivot bracket 150 relative to the lower pivot bracket 152. The pivoting action of the upper pivot bracket 150 relative to the lower pivot bracket 152 permits the pelvic support brace 21 to be pivotable between a first, neutral position and a second, tilted position, such as the two positions described in the '558 patent. The rubber spring 154 is flexible enough to allow this pivoting, but its bias to a relaxed state resists this movement, providing some support for an individual in the pelvic stabilization device 20. In addition, the tendency of the rubber spring 154 to return a relaxed state provides a bias to return the pelvic support brace 21 to the first, neutral position from the second, tilted position. The structure and function of the upper pivot bracket 150, the rubber spring 154, and the lower pivot bracket 152 are further described below.

Figure 11:
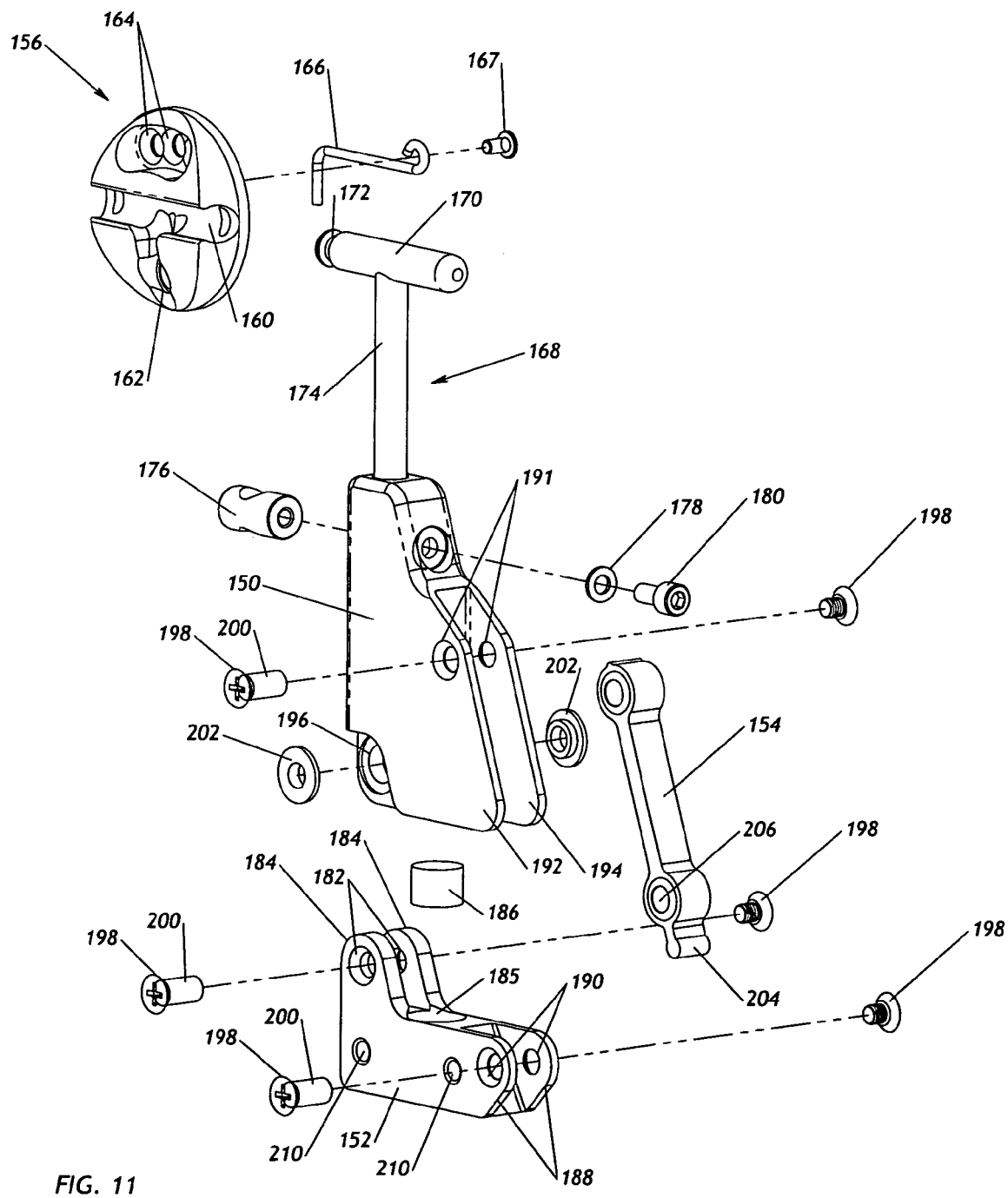
FIG. 11 is an exploded side perspective view of the pivoting side mount of FIG. 9.
Figure 12:
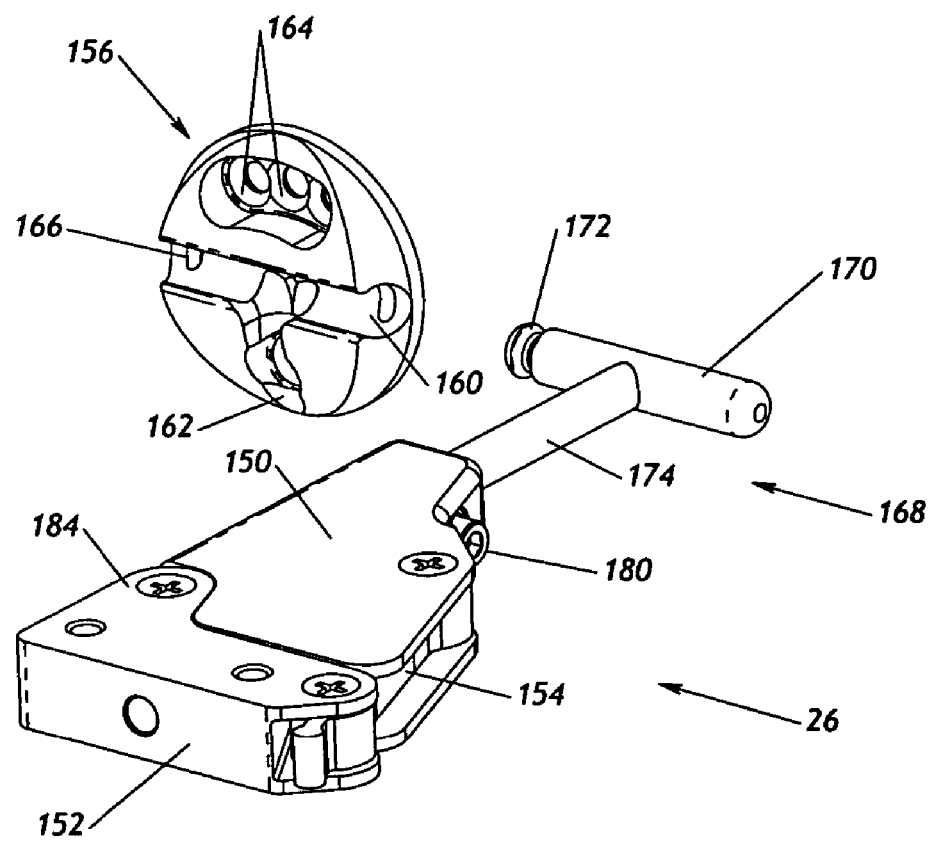
FIG. 12 is a side perspective view of a beginning stage of assembly of the pivoting side mount of FIG. 9.

A mounting plate 156 is provided for attaching the pivoting side mount 26 to the pelvic support brace 21. The mounting plate 156 shown in the drawings includes a round groove 160 extending horizontally through its length, and a downward slot 162 in communication with the round groove 160. Mounting holes 164 are provided for attaching the mounting plate 156 to the pelvic support brace 21, for example by fasteners (not shown). As can be seen in FIG. 11, in accordance with an embodiment, a detent spring 166 is provided that attaches on the back side of the mounting plate 156. The detent spring 166 is attached, for example, by a fastener 167 and is arranged so that a portion of the detent spring extends through an oblong slot in the round groove 160 on the front of the mounting plate 156, as shown in FIG. 12.

A T-bar 168 extends between the upper pivot bracket 150 and the mounting plate 156. The T-bar 168 includes an upper bar 170 that extends horizontally. The upper bar 170 includes a groove 172 at one end. A height adjustment bar 174 extends downward from the upper bar 170, from the center of the upper bar 170.

The T-bar 168 is attached to the upper pivot bracket 150 by a barrel nut 176, a washer 178, and a screw 180. Tightening of the screw 180 causes the barrel nut 176 to trap a section of the height adjustment bar 174 against the inner portion of the upper pivot bracket 150, locking the T-bar 168 into place. Prior to tightening of the T-bar 168, the height adjustment bar 174 is free to rotate within, and/or move up and down within, the upper pivot bracket 150.

Details of the lower pivot bracket 152 can be seen in FIG. 11. The lower pivot bracket 152 includes pivot holes 182 extending through rear flanges 184. The rear flanges 184 extend upward from a rear portion of the lower pivot bracket 152. A seat 185 is located just forward of the rear flanges 184 and receives a rubber cylindrical bumper 186.

Front flanges 188 extend out of the front end of the lower pivot bracket 152 and include rubber spring mounting holes 190 therethrough. Similar rubber spring mounting holes 191 are positioned about halfway up the front portion of the upper pivot bracket 150. The rubber spring mounting holes 191 on the upper pivot bracket 150 extend through two opposing walls 192, 194.

To attach the lower pivot bracket 152 to the upper pivot bracket 150, a pivot member is positioned in the pivot holes 182 and extends through an opening 196 on the bottom of the upper pivot bracket 150. The pivot member may be formed by, for example, screws 198 and threaded standoffs 200. The threaded standoffs 200 are cylinders with internal threads on opposite sides so that a pair of screws, e.g., the screws 198 may be threaded into opposite sides of the threaded standoffs 200 and thus the threaded standoffs 200 serves as a spacer between the two screws 198. Washers 202 may also be used in the connection. The connection is preferably made so that the lower pivot bracket 152 is free to pivot relative to the upper pivot bracket 150 about the connection at the pivot holes 182 and the opening 196.

The rubber spring 154 is then attached to the upper pivot bracket 150 and the lower pivot bracket 152. Initially, the upper end of the rubber spring 154 is attached, for example, by additional screws 198 and threaded standoffs 200 to the rubber spring holes 191 on the upper pivot bracket 150 and passing through an upper hole of the rubber spring. The opposing walls 192, 194 are preferably spaced and the connection of the upper end of the rubber spring 154 is preferably made such that the rubber spring 154 is free for rotation about the connection at the rubber spring holes 191.

The lower end of the rubber spring 154 is then attached to the front end of the lower pivot bracket 152. To aid in this assembly, a tab 204 is provided at the bottom end of the rubber spring 154. The tab 204 permits a assembler to grasp the end of the rubber spring 154, for example by using a pair of pliers, to pull the rubber spring 154 to align a lower opening 206 on the rubber spring 154 with the rubber spring mounting holes 190. Again, the attachment may be made with screws 198 and threaded standoffs 200, although other mechanisms may be used. In any event, the rubber spring 154 is preferably rotatable relative to its mounting at the rubber spring mounting holes 190.

The lower pivot bracket 152 includes mounting holes 210 extending therethrough. The mounting holes 210 may be used to attach the lower pivot bracket 152 to a suitable structure. For example, in the embodiment shown in FIG. 1, fasteners may be used to attach the body 40 to the adapter plate 220. In such an embodiment, fasteners, such as screws or bolts, may extend through the adapter plate and into the mounting holes 210 on the lower pivot bracket 152. In this embodiment, the mounting holes 210 are threaded to receive the screws. Alternatively, the lower pivot bracket 152 may connect directly to the fasteners 55 in the body 28. In this alternate embodiment, bolts or screws may extend through the mounting holes 210 and into the fasteners 55. Other suitable mounting arrangements may be provided.

Figure 13:
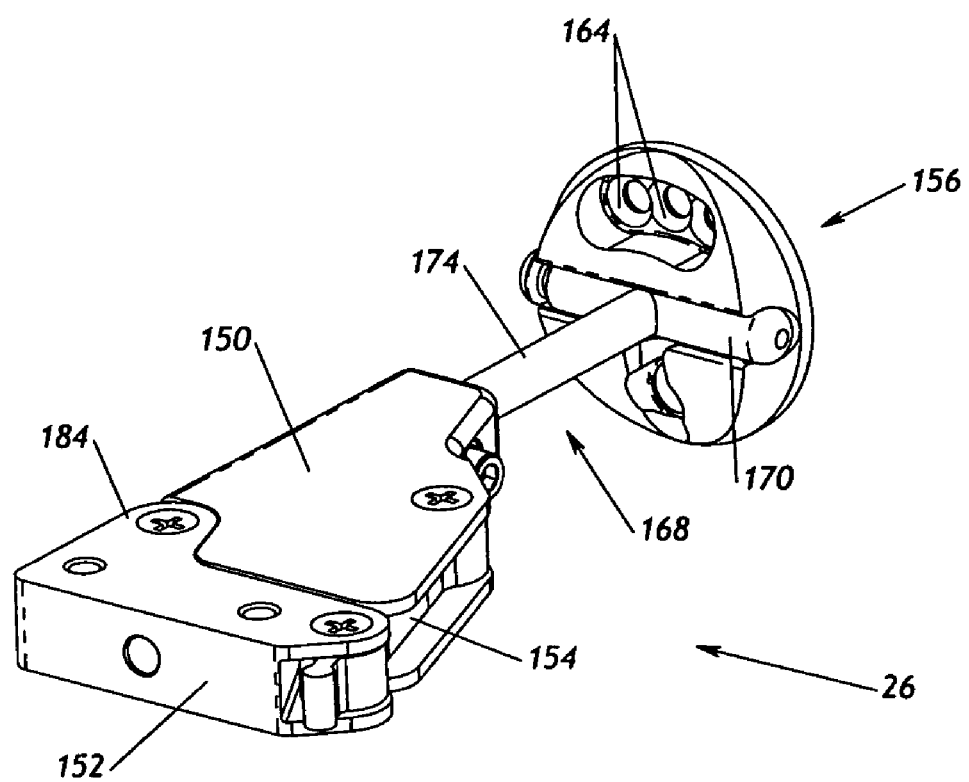
FIG. 13 is a further stage of assembly of the pivoting side mount of FIG. 9.

The installation process for the pivoting side mount 26 is shown in FIGS. 12 and 13. Initially, the mounting plate 156 is attached to a suitable structure, in the embodiment shown the pelvic support brace 21. The pivoting side mount 26 may then be attached to the mounting plate 156. First, the upper bar 170 is aligned with the round groove 160 on the mounting plate 156, as is shown in FIG. 12. The upper bar 170 is then moved sideways, to the left in FIG. 12, so that the upper bar 170 is received within the round groove 160. The upper bar 170 is continually pushed in this direction until the groove 172 aligns with and is engaged by the detent spring 166. This engagement prevents the T-bar 168 from slipping loosely out of position, and also serves as an indicator for proper orientation when attaching the pivoting side mount 26 to the mounting plate 156.

In an embodiment, the groove 172 is asymmetrical, allowing easy insertion into the round groove 60, but preventing overtravel past the detent spring 166. The detent spring 166 engages in the groove 172 and aligns the height adjustment bar 174 with the downward slot 162 on the mounting plate 156, as is shown in FIG. 13.

The pivoting side mount 26 may then be rotated downward from the position in FIG. 13 to the position in FIG. 9. Rotating the pivoting side mount 26 in this manner causes the upper portion of the height adjustment bar 174 to be received within the downward slot 162, and locks the pivoting side mount 26 from fore and aft movement relative to the mounting plate 156.

The fact that the height adjustment bar 174 is round and that the T-bar 168 is attached in a pivoting manner to the mounting plate 156 permits compensation from misalignment of attachment of the pivoting side mount 26 in three axes. That is, by loosening the barrel nut 176, the pivoting side mount 26 may be adjusted relative to the mounting plate 156 in two dimensions (up and down and rotation), and the pivoting side mount 26 may swing outward from the mounting plate 156 by moving slightly out of the downward slot 162. Misalignment compensation provides many advantages. It permits the user to join a pelvic support brace to, for example, wheelchairs of very different widths. Furthermore, it allows the pelvic support brace to be adjusted asymmetrically relative to the wheelchair to fit users with deformity or pelvic tilt, pelvic rotation, or pelvic obliquity.

The T-bar and mounting plate connection may be used for other structures. For example, the T-bar/mounting plate connection may be used anywhere a detachable plate is needed.

In the embodiment shown in FIG. 1, after the T-bar 168 has been attached to the mounting plate 156, the bodies 40 may be inserted into the receivers 30. The pivoting side mount 26 is then fully attached to the wheelchair via the wheelchair side bars 22, 24.

In a normal, neutral position, the upper pivot bracket 150 is positioned as shown in FIG. 9 relative to the lower pivot bracket 152. The rubber spring 154 pulls the front end of the upper pivot bracket 150 downward relative to the lower pivot bracket 152, and the lower portion of the upper pivot bracket 150 engages the rubber cylindrical bumper 186 to prevent further travel. To this end, the rubber spring 154 pre-tensions the upper pivot bracket 150 downward in the position shown in FIG. 9.

The rubber cylindrical bumper 186 is slightly compressible, allowing the upper pivot bracket 150 to tilt negative, or backward, relative to a person sitting in a wheelchair and held by the pelvic stabilization device 20, providing comfort for a user leaning into the pelvic support brace 21.

Figure 10:
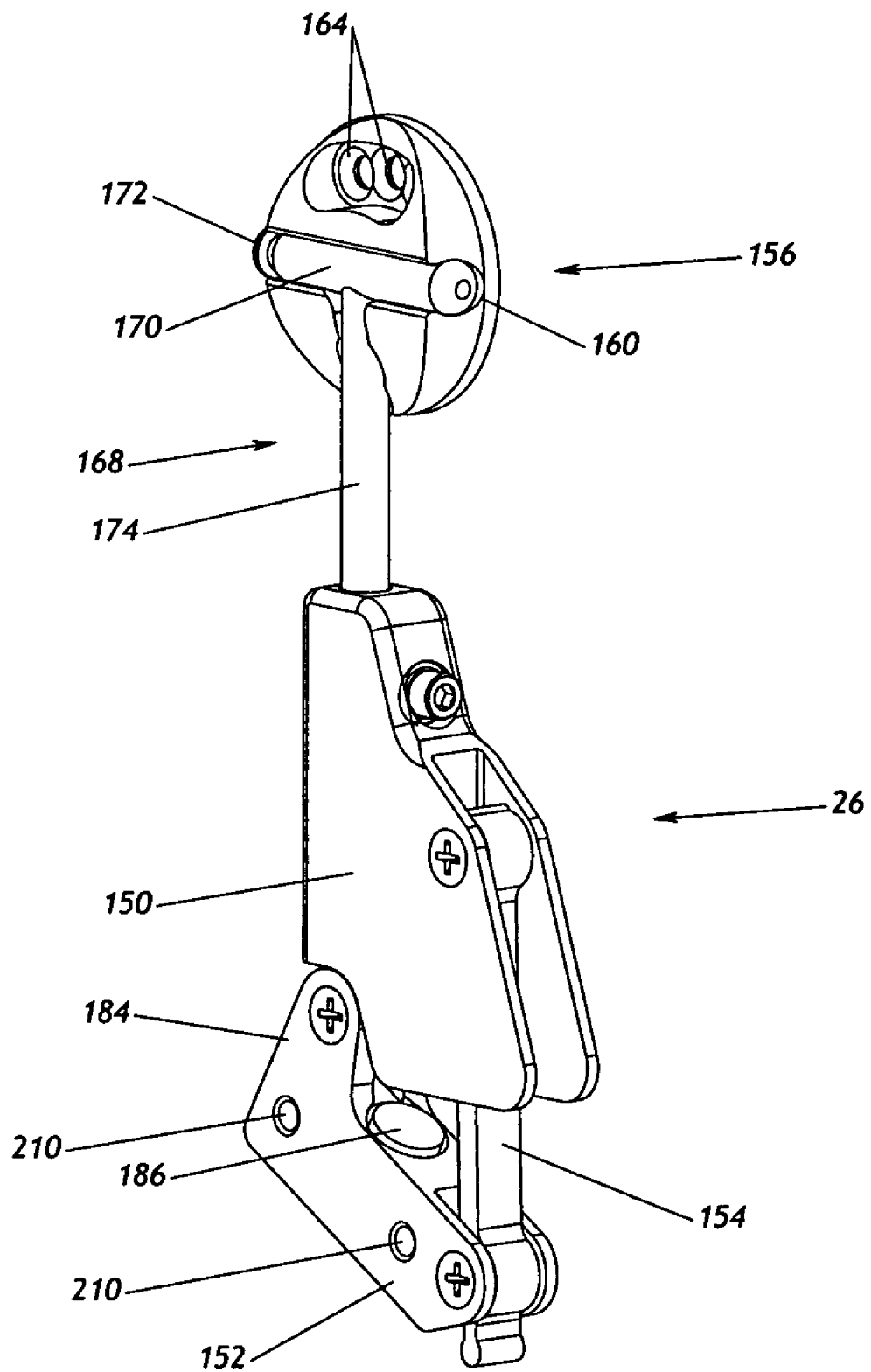
FIG. 10 is a side perspective view of the pivoting side mount of FIG. 9, with a lower pivot bracket rotated relative to an upper pivot bracket.

A user attached to the pelvic support brace 21 may lean forward against the bias of the rubber spring 154. The pivoting side mount 26 moves to the position shown in FIG. 10 against the bias of the rubber spring 154. The bias of the rubber spring 154 limits this forward movement. To this end, a particular rubber spring 154 may be selected according to the weight and ambulation of a user. In addition, the pivoting side mount 26 provides easy removal and installation of additional or different rubber springs 154.

Although described with reference to a rubber spring 154, the rubber spring may be any device providing a spring function or bias against pivoting of the upper pivot bracket 150 relative to the lower pivot bracket 152. Examples include, but are not limited to, elastomers, coil springs, and composite materials that resist bending.

In accordance with an embodiment, the rubber spring 154 pivots freely at each end without friction from the opposing walls 192, 194 or the front flanges 188. The pivoting attachment of the ends of the rubber spring 154 also aids in this function. To this end, the rubber spring 154 acts as a flexible resilient band without additional friction, prolonging its useful life.

Moreover, the rubber spring 154 is shielded from external damage by the distal ends of the opposing walls 192, 194 and the front flanges 188. Both the opposing walls 192, 194 and the flanges 188 preferably extend beyond the rubber spring 154 in the relaxed and extended positions.

The cylindrical rubber bumper 186 provides an additional function in that it cushions the return of a user from a leaning forward position to the neutral position. A bumper may be made of materials other than rubber that provide this function, and a particular rubber or other material may be provided to provide more or less cushion.

The combined pivoting side mount 26 and quick release assembly 28 provide a quick and easy manner in which to attach a device, such as the pelvic support brace 21, to a wheelchair or other structure. A user may attach the pivoting side mount 26 to the pelvic support brace 21 and then attach the pivoting side mount 26 to a wheelchair or other structure without the use of tools. In addition, the pivoting side mount 26 and the pelvic support brace 21 may very easily be removed without tools.

Figure 14:
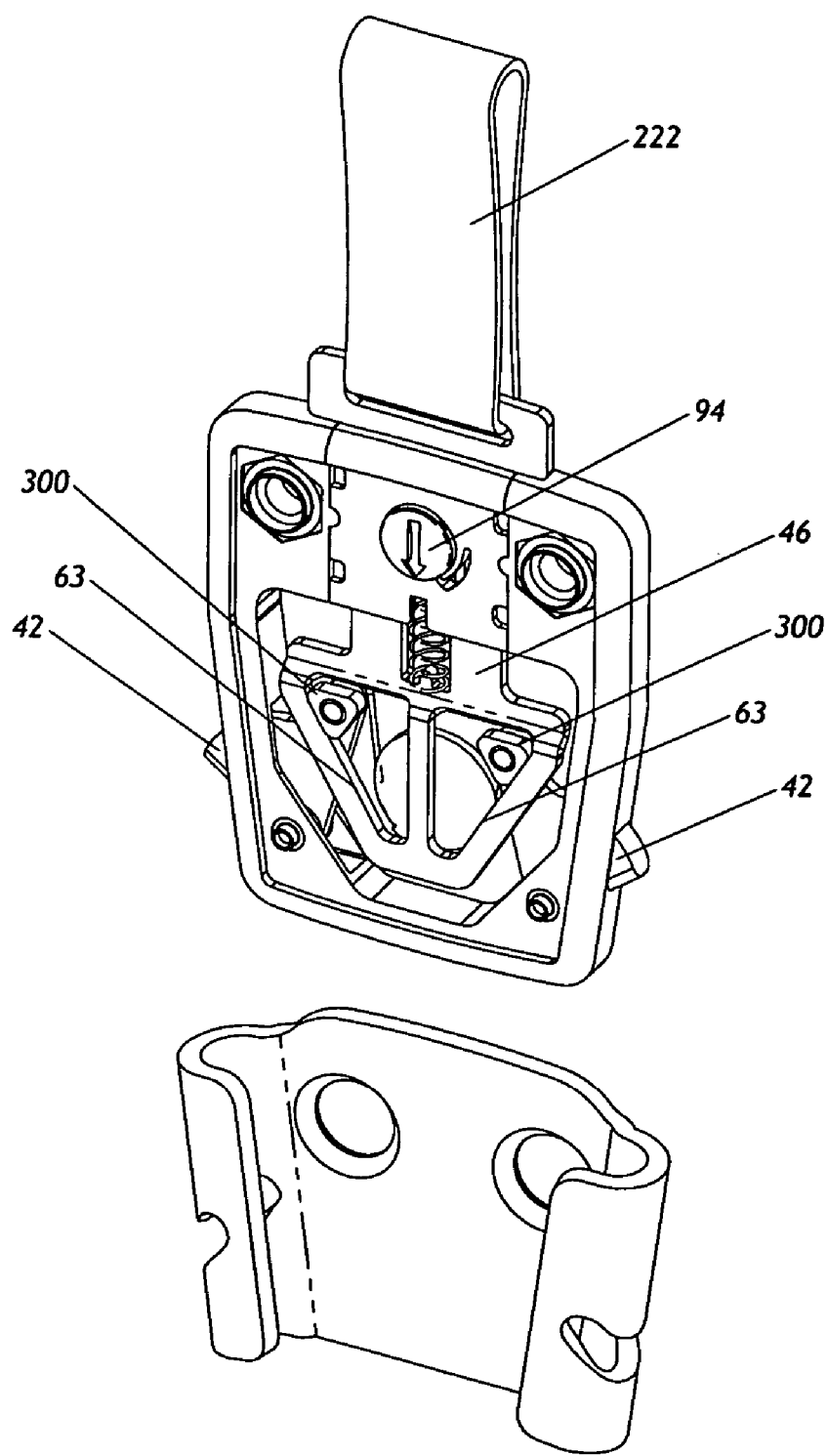
FIG. 14 shows a perspective view of an alternate embodiment of a quick release assembly in accordance with an embodiment of the invention.

FIG. 14 shows an alternate embodiment of a quick release assembly. The embodiment shown includes many of the same parts as the previously described embodiment. However, instead of the pins 82 engaging the slanted inner cam surfaces 63, low friction blocks 300 are attached to the latches 42. The low friction blocks 300 reduce wear and galling between the latches 42 and the sliding release plate 46. In an embodiment, the low friction blocks 300 are triangular in shape, but other configurations may be used. Because of the generally triangular shape of the openings 62, a similar triangular shape for the low friction blocks 300 provides an exemplary contact area with the cam surfaces 63. Increasing the contact area reduces contact stresses so that softer low friction materials may be used without risk of deformation, as would be the case with a round shape. Furthermore, in accordance with an embodiment, the low friction blocks 300 are shaped as an equilateral triangle. As such, they may be easily assembled in any position of rotation on the axis of the pins 82 with no change in function. In addition, although the shown embodiment utilizes a low friction material for the cam surface of the latches 42, in an alternate embodiment, low friction material may be used on the sliding release plate 46 instead of, or in addition to, the low friction material used for the low friction blocks 300.

In an embodiment, the low friction material used for the low friction blocks 300 comprises POM acetal resin (Polyoxymethylene), although other materials may be used. POM acetal resin is a rugged polymer that serves as an excellent choice for long-term mechanical stability.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A quick release assembly, comprising:
   a receiver having at least one protrusion, the receiver having an opening having an elongate cross section;
   a body that is configured to be received within the opening of the receiver, the body inserting into the receiver in an insert direction, the body comprising four body contact surfaces and one or more latches, each latch corresponding to a respective protrusion of said at least one protrusion on the receiver, and each latch being rotatably mounted and comprising a rounded outer surface that is biased in a latch direction so that a portion of the rounded surface latches behind one of said at least one protrusion when the body is received within the receiver, the four body contact surfaces being tapered outward from an insert end of the body;
   the receiver having four receiver contact surfaces that align against the four body contact surfaces when the body is inserted into the receiver, the four receiver contact surfaces being tapered in a similar manner to the four body contact surfaces to cause two-directional wedging of the body in the receiver such that play is eliminated in both a fore to aft direction and a left to right direction when the body is inserted into the receiver, the fore to aft direction, left to right direction, and insert direction being mutually and substantially perpendicular; and
   a release mechanism for releasing said one or more latches from the protrusions wherein:
   the body is inserted into the receiver moving in a direction from a first end toward a second end;
   each said one or more latches is rotatably mounted about a rotational mount and the rounded outer surface of the latch defines a cam surface having an outward end and an inward end, the latch moving in a direction from the inward end toward the outward end to latch a respective protrusion; and
   for each latch, a portion of the rounded outer surface of the latch extending beyond a respective protrusion in the latch direction slants downward toward the rotational mount and toward the second end from the inward end toward the outward end so that the distance from the cam surface to the rotational mount decreases from the inner end to the outward end of the cam surface.

2. The quick release assembly of claim 1, wherein the receiver comprises rounded side channels, and wherein each said at least one protrusion comprises a notch in the rounded side channels.

3. The quick release assembly of claim 2, wherein the body is received within the receiver from a first end toward a second end, and wherein the second end of the receiver is open.

4. The quick release assembly of claim 2, wherein the receiver comprises a plate with two curled edges which receive outer edges of the body, and wherein each notch is located in a curled edge.

5. The quick release assembly of claim 4, wherein the receiver contact surfaces are located in the curled edges.

6. The quick release assembly of claim 5, wherein the outer edges of the body are radiused to substantially match the curled edges of the receiver, and wherein the radiused edges of the body are flattened at the extreme edges.

7. The quick release assembly of claim 1, wherein the body fits into the receiver from a first end toward a second end, and wherein the second end of the receiver is open.

8. The quick release assembly of claim 1, wherein the release mechanism moves from a first position to a second position to release said one or more latches from the protrusions, and further comprising a lock which prevents undesired movement of the release mechanism to the second position, said lock alternately blocking or permitting movement of the release mechanism to the second position.

9. The quick release assembly of claim 8, wherein the lock comprises a protrusion that in a first arrangement blocks movement of the release mechanism to the second position, and in a second arrangement allows movement of the release mechanism, and wherein the lock is moved from the first arrangement to the second arrangement by pressing in and rotating a button on the quick release assembly.

10. The quick release assembly of claim 1, wherein the latches are movable to latch against the protrusions independent of the release mechanism, and wherein the release mechanism comprises a cam surface aligned to engage each of said one or more latches, and wherein actuation of the release mechanism causes the cam surface to engage said one or more latches to remove said one or more latches from behind said at least one protrusion when the body is fitted into the receiver.

11. A quick release assembly, comprising:
   a receiver comprising an insert end and a second end opposite the insert end and an axis defined between the second and the insert end;
   at least one protrusion defined in said receiver;
   a body that is configured to be received within the receiver by inserting into the insert end toward the second end, the body comprising one or more latches, each latch corresponding to a respective said at least one protrusion and comprising an outer surface that is biased in a latch direction so that a portion of the outer surface latches behind one of said at least one protrusions when the body is fitted into the receiver, each latch comprising a cam follower; and
   a release mechanism mounted to the body and for sliding movement relative to the body, the release mechanism comprising at least one cam surface, the release mechanism being arranged and configured such that when the body is inserted in the receiver, pulling on the release mechanism in a direction along the axis from the second end towards the insert end causes a corresponding movement of said at least one cam surface along the axis, causing said at least one cam surface to engage the cam follower on said one or more latches, releasing said one or more latches from the protrusions, wherein each latch is movable to latch against a respective protrusion independent of the release mechanism.

12. The quick release assembly of claim 11, wherein the release mechanism comprises a release plate that is slidingly mounted in the body and on which said at least one cam surface is mounted, the cam surface being slanted relative to a longitudinal axis of the release mechanism so that the cam follower moves perpendicular to the longitudinal axis when the release mechanism is moved in the direction and the cam follower engages the cam surface.

13. The quick release assembly of claim 12, wherein said at least one cam surface is defined by at least one inner surface of at least one opening in the release plate.

14. The quick release assembly of claim 12, wherein the release mechanism moves from a first position to a second position to release said one or more latches from the protrusions, and further comprising a lock which prevents undesired movement of the release mechanism to the second position, said lock alternately blocking or permitting movement of the release mechanism to the second position.

15. The quick release assembly of claim 14, wherein the lock comprises a protrusion that in a first arrangement blocks movement of the release mechanism to the second position, and in a second arrangement allows movement of the release mechanism, and wherein the lock is moved from the first arrangement to the second arrangement by pressing in and rotating a button on the quick release assembly.

16. The quick release assembly of claim 15, wherein at least one of said at least one cam surface and the cam follower comprises a low friction block.

17. A quick release assembly, comprising:
a receiver defining an upwardly-oriented opening and comprising an insert end and a second end opposite the insert end and first and second sides;
a first protrusion defined in the first side;
a body that is configured to be received within the receiver by inserting the body into the insert end in a direction toward the second end, the body comprising:
a first latch rotatably mounted to the body at a first rotational mount and comprising a first rounded outer cam surface opposite the first rotational mount, the first rounded outer cam surface defining an outward end and an inward end, and slanting downward toward the rotational mount and the second end from the inward end toward the outward end so that the distance from the first rounded outer cam surface to the rotational mount decreases from an inner portion to an outer portion of the rounded outer cam surface, the latch moving in a first latch direction from the inward end toward the outward end to latch a respective protrusion, the first latch being biased outward relative to the body in the first latch direction and being positioned and arranged so that a portion of the first outer cam surface latches behind the first protrusion when the body is fitted into the receiver, and the first rotational mount being located away from the first side of the receiver relative to the first protrusion when the body is fitted into the receiver; and
a release mechanism for releasing the first latch from the first protrusion.

18. The quick release assembly of claim 17, wherein the first latch is movable to latch against the first protrusion independent of the release mechanism.

19. The quick release assembly of claim 18, wherein the release mechanism comprises a release plate that is slidingly mounted in the body so as to be movable from a first position to a second position, the release mechanism comprising a cam surface for engaging the first latch and removing the latch from against the first protrusion as the release mechanism moves from the first position to the second position.

20. The quick release assembly of claim 19, further comprising a lock which prevents undesired release of the body from the receiver, the lock requiring two separate and different actions to release the body from the receiver.

21. The quick release assembly of claim 20, wherein the lock prevents the release plate from sliding relative to the body.

22. A quick release assembly, comprising:
a receiver having at least one protrusion;
a body that is configured to be received within the receiver, the body comprising one or more latches, each latch corresponding to a respective protrusion of said at least one protrusion on the receiver, and each latch being rotably mounted and comprising a rounded outer surface that is biased in a latch direction so that a portion of the rounded surface latches behind one said at least one protrusions when the body is received within the receiver;
a release mechanism for releasing said one or more latches from the protrusions, wherein the release mechanism moves from a first position to second position to release said one or more latches from the protrusions; and
a lock which prevents undesired release of the body from the receiver, the lock alternately blocking or permitting movement of the release mechanism to the second position, the lock comprising a protrusion that in a first arrangement engages and blocks movement of the release mechanism to the second position, and in a second arrangement is removed from the path of, and allows movement of the release mechanism, and wherein the lock comprises a button mounted for rotation in the body, the button being connected to the protrusion of the lock and comprising a outer push surface engagable by a user's finger, and the lock is moved from the first arrangement to the second arrangement by a user's finger pressing in and rotating the button on the quick release assembly.

23. The quick release assembly of claim 22, wherein the lock, when engaged, prevents movement of the release mechanism a sufficient amount to release the latches from the protrusions of the receiver.

* * * * *